(12) United States Patent
Meads et al.

(10) Patent No.: US 10,487,286 B2
(45) Date of Patent: Nov. 26, 2019

(54) HIGHLY BORATED DISPERSANT CONCENTRATES FOR LUBRICATING OIL COMPOSITIONS AND METHODS FOR FORMING SAME

(71) Applicant: Infineum International Limited, Abingdon (GB)

(72) Inventors: Marc W. Meads, Wantage (GB); Jacob Emert, Brooklyn, NY (US); Jun Hua, Highland Park, NJ (US)

(73) Assignee: INFINEUM INTERNATIONAL LTD., Abingdon, Oxfordshire (GB)

( * ) Notice: Subject to any disclaimer, the term of this patent is extended or adjusted under 35 U.S.C. 154(b) by 0 days.

(21) Appl. No.: 15/161,523

(22) Filed: May 23, 2016

(65) Prior Publication Data
US 2017/0335226 A1  Nov. 23, 2017

(51) Int. Cl.
*C10M 139/00* (2006.01)
*C10N 30/04* (2006.01)
*C10N 40/25* (2006.01)

(52) U.S. Cl.
CPC ...... *C10M 139/00* (2013.01); *C10M 2227/00* (2013.01); *C10N 2030/04* (2013.01); *C10N 2040/25* (2013.01); *C10N 2230/04* (2013.01); *C10N 2240/10* (2013.01)

(58) Field of Classification Search
CPC combination set(s) only.
See application file for complete search history.

(56) References Cited

U.S. PATENT DOCUMENTS

| | | | |
|---|---|---|---|
| 2,813,830 A | 11/1957 | Trautman | |
| 3,014,061 A | 12/1961 | Irish | |
| 3,087,936 A | 4/1963 | Le Suer | |
| 3,185,644 A | 5/1965 | Knowles | |
| 3,224,971 A | 12/1965 | Knowles | |
| 3,254,025 A * | 5/1966 | Le Suer | C07C 243/00 44/317 |
| 3,347,793 A | 10/1967 | Washburn | |
| 3,509,054 A | 4/1970 | Hinkamp | |
| 3,829,381 A | 8/1974 | Le Suer | |
| 3,928,216 A | 12/1975 | Saunders et al. | |
| 4,092,127 A | 5/1978 | Ryer et al. | |
| 4,657,686 A | 4/1987 | Holstedt et al. | |
| 4,724,099 A | 2/1988 | Holstedt et al. | |
| 4,756,842 A | 7/1988 | Holstedt et al. | |
| 5,583,099 A | 12/1996 | Steckel | |
| 2008/0194438 A1 * | 8/2008 | Bera | C08F 283/00 508/110 |
| 2010/0152073 A1 * | 6/2010 | Nelson | C10M 141/12 508/108 |

FOREIGN PATENT DOCUMENTS

| | | |
|---|---|---|
| EP | 0089844 B1 | 12/1985 |
| EP | 0499384 A1 | 8/1992 |
| EP | 0499384 B1 | 6/1995 |
| GB | 1086692 A | 10/1967 |

OTHER PUBLICATIONS

W.W. Yau, J.J. Kirkland, and D.D. Bly, Modern Size-Exclusion Liquid Chromotography, E. I. duPont de Nemours & Co., 1979, p. 4-14, John Wiley & Sons, Wilmington, DE.

* cited by examiner

*Primary Examiner* — Prem C Singh
*Assistant Examiner* — Chantel L Graham

(57) ABSTRACT

A process for producing a borated polyalkenyl succinimide dispersant composition in which the boron is incorporated primarily as cyclic metaboric acid moieties and the equivalents of boron incorporated per equivalent of nitrogen in the succinimide carrier is greater than 2; in which process a slurry of orthoboric acid is added to a polyalkenyl succinimide to form a reaction mixture, which reaction mixture is then heated under conditions (at a temperature and pressure and for a time) sufficient to remove from the reaction mixture from about 0.8 to about 1.2 moles of water of reaction per mole of boric acid charged.

42 Claims, No Drawings

HIGHLY BORATED DISPERSANT CONCENTRATES FOR LUBRICATING OIL COMPOSITIONS AND METHODS FOR FORMING SAME

The present invention relates to highly borated nitrogen-containing dispersant concentrates for lubricating oil compositions, and methods for forming same. More particularly, the present invention is directed to borated nitrogen-containing dispersant concentrates, such as borated succinimide dispersant concentrates, having a boron to nitrogen (B:N) ratio of greater than about 2, and a reduced level of associated sediment, and a method for forming such borated dispersants concentrates, preferably without the need for filtration.

BACKGROUND OF THE INVENTION

The trend in the automotive industry to simultaneously move to higher efficiency, hotter-running engines and lower viscosity lubricants for fuel economy has led to durability challenges in both passenger car and heavy duty diesel engine applications. One approach taken to enhance the durability of these engines has been to incorporate boron into the lubricant. Boron-containing fluids have a history of exhibiting oxidation inhibition and anti-wear properties in a range of environments (U.S. Pat. Nos. 4,724,099, 3,224,971, 3,185,644, 4,756,842, 4,657,686, 3,014,061, 2,813,830). Boron can be introduced in significant amounts via small molecules (e.g. boron esters, EP0089844, GB434626, U.S. Pat. Nos. 3,347,793, 3,509,054, FR1203698), however, incorporation of these materials into lubricants can cause adverse side effects, such as corrosion issues and phase separation. Boron can also be introduced via additive carriers such as dispersants or detergents (U.S. Pat. No. 3,087,936, GB1086692, U.S. Pat. Nos. 3,829,381, 3,928,216). However, the amount of boron introduced by such carriers needs to be matched with the amount of carrier. For high boron concentrations, the required large amount of carrier (associated dispersant or detergent) can lead to an inordinately high viscometric contribution, which adversely impacts base stock flexibility. A solution to this problem would be to prepare a boron carrier, specifically a borated dispersant concentrate, with very high boron content that could be used broadly in a range of applications without significantly impacting fluid viscometrics or additive treat rates.

Historically, such borated dispersant concentrates are known where the total nitrogen to boron molar ratio is in the range 4:1-1:2 (U.S. Pat. No. 5,583,099; 1:1-1:1.25 in examples) with preferred ratios containing an excess of nitrogen or being close to stoichiometric (e.g. 2:1-1:1). Borated dispersant concentrates are typically prepared by reacting boric acid with a range of dispersant types while sweeping out water. It is believed that during the boration process, boric acid dehydrates to cyclic metaboric acid (Structure I, shown below) leading to the evolution of water. The oil-insoluble metaboric acid is solubilized in the dispersant concentrate by interaction with the basic nitrogens on the dispersant. The products of the invention disclosed in U.S. Pat. No. 5,583,099 are prepared by reacting boric acid with a dispersant compound containing an amide, imide or Mannich base group having present at least one amine group or salt thereof, in the presence of a protic compound, in a weight ratio to boric acid of at least about 1:2.

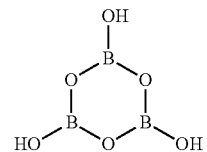

Structure I

Highly borated dispersant concentrates are described where the boron to total nitrogen weight ratio is in the range of about 0.2 to about 65 (EP0499384A1); corresponding to a nitrogen to boron molar ratio of about 0.15 to about 50.3. The polybutene of the succinimide had an $M_n$ within the range of 900 to 3000 daltons, with a most preferred range of 1200 to 2300 daltons. The boron-containing moiety of this borated succinimide was a boron oxide $(B_xO_y)_z$ wherein x and y are 1 to 3 and z is 2 to 56. The process used to incorporate the boron utilized a very high temperature (170 to 260° C.; preferably 182 to 218° C., e.g., 182 to 193° C. in order to completely dehydrate the orthoboric acid to boron oxide ($B_2O_3$, Structure II). The eliminated water collected using a Dean and Stark apparatus corresponded to more than 1.5 mole of water per mole of boric acid charged, which supports the position that boron is present in the product in the form of boron oxide. Using this approach, the efficiency of the boron incorporation is relatively low (about 50 to 90%), resulting in compositions having significant amounts of sediment that has to be removed using filtration.

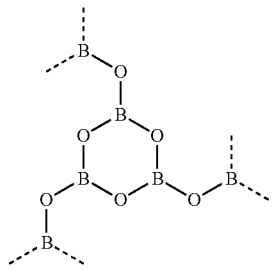

Structure II

SUMMARY OF THE INVENTION

In accordance with a first aspect of the invention, there is provided a process for producing a borated polyalkenyl succinimide dispersant composition in which the boron is incorporated primarily as cyclic metaboric acid moieties and the equivalents of boron incorporated per equivalent of nitrogen in the succinimide carrier is greater than 2; in which process a slurry of boric acid comprising primarily of orthoboric acid in a substantially non-protic hydrocarbon medium is added to a polyalkenyl succinimide in a substantially non-protic hydrocarbon medium to form a reaction mixture, which reaction mixture is then heated under conditions (at a temperature and pressure and for a time) sufficient to remove from the reaction mixture from about 0.8 to about 1.2 moles of water of reaction per mole of boric acid charged.

In a second aspect of the invention, there is provided a borated polyalkenyl succinimide dispersant produced by the process of the first aspect.

In a third aspect of the invention, there is provided a lubricating oil composition comprising a borated polyalkenyl succinimide dispersant of the second aspect, in an amount contributing from about 20 to about 600 ppm of boron to the composition.

Other and further objectives, advantages and features of the present invention will be understood by reference to the following specification.

DETAILED DESCRIPTION OF THE INVENTION

The present invention is directed to borated succinimide dispersant concentrates having a high boron content (and high B:N ratio), and a process that allows for the preparation of borated succinimide dispersant concentrates having a high boron content (and high B:N ratio), without the need of a filtration step to remove sediment. Specifically, the present invention is directed to a process for forming a highly concentrated, low sediment borated dispersant composition in which the boron is incorporated primarily as cyclic metaboric acid moieties ($B_3O_3(OH)_3$, Structure I) rather than boric oxide (Structure II), as evidenced by amount of collected water distillate (from about 0.8 to about 1.2 moles of water of reaction per equivalent of boron, ideally, about 1 mole water per equivalent of boron), and the equivalents of boron incorporated per equivalent of total nitrogen in the succinimide carrier is greater than 2. The process of the present invention allows for the preparation of unique, low sediment, highly borated polyalkenyl succinimide dispersant products.

More specifically, the present invention is directed to the discovery that, by appropriate selection of the dispersant structure and boration process, a low sediment, highly borated dispersant concentrate can be produced in which the boron is incorporated largely as cyclic metaboric acid moieties ($B_3O_3(OH)_3$, (Structure I) rather than boron oxide, yet the equivalents of boron incorporated per equivalent of nitrogen in the succinimide dispersant carrier is greater than 2. With the specified dispersant structure and boration process, the equivalents of boron per equivalent of basic nitrogen incorporated into the borated dispersant concentrate can exceed 3:1. That such a borated dispersant could be produced is surprising as the oil-insoluble metaboric acid would be expected to be solubilized in the dispersant concentrate by interaction with the basic nitrogens of the dispersant and the maximum expected stoichiometry of boron to basic nitrogen would be 3:1 (1 metaboric acid moiety per basic nitrogen). The greater than stoichiometric incorporation of boron therefore suggests that unique structures are formed whereby more boron is solubilized than could be accommodated by interaction of every basic nitrogen of the dispersant with a metaboric acid moiety. The benefit of these high boron, no sediment compositions is that no filtration is required and the carrier has a reduced viscometric contribution for a given target boron content in a lubricant formulation.

Although the dispersants used to prepare the borated dispersants of the prior art included a broad range of polymer molecular weight and head group structures, the succinimide dispersant structure required to provide the composition of the present invention is limited to polyalkenyl succinimides derived from the reaction of a polyalkenyl succinic acylating agent derived from a polyalkene having a number average molecular weight (Mn) of at least about 700, more preferably at least about 800 daltons, and a number average molecular weight (Mn) of no greater than about 1600, such as no greater than about 1400, preferably no greater than about 1250 daltons. Preferably, the succinimide dispersant structure used to provide the composition of the present invention is a polyalkenyl succinimide derived from the reaction of a polyalkenyl succinic acylating agent derived from a polyalkene having a number average molecular weight (Mn) of from about 700 to about 1600 daltons, preferably from about 700 to about 1400 daltons, more preferably from about 800 to about 1250 daltons; and a polyamine or polyamine mixture, which polyamine or polyamine mixture has, or has on average, from about 5 to about 8 nitrogen atoms per molecule, preferably from about 6 to about 7 nitrogen atoms per molecule, whereby the succinic to primary amine stoichiometric ratio (sometimes referred to as "coupling ratio") of the resulting succinimide dispersant is no greater than about 13.

Polymer molecular weight, specifically $M_n$, can be determined by various known techniques. One convenient method is gel permeation chromatography (GPC), which additionally provides molecular weight distribution information (see W. W. Yau, J. J. Kirkland and D. D. Bly, "Modern Size Exclusion Liquid Chromatography", John Wiley and Sons, New York, 1979). Another useful method for determining molecular weight, particularly for lower molecular weight polymers, is vapor pressure osmometry (see, e.g., ASTM D3592).

Preferably, the polyalkenyl succinimides used in the process of the present invention have a coupling ratio of from about 0.8 to about 1.3, preferably from about 0.9 to about 1.2, most preferably from about 0.9 to about 1.1, wherein, again, "coupling ratio" is defined as a ratio of succinyl groups in the polyalkenyl succinic acylating agent to primary amine groups in the polyamine reactant. At a coupling ratio of less than 1, there will be free polyamine reactant associated with the succinimide product. At a coupling ratio of greater than 1, some polyamine will react with free polyalkenyl succinic acylating agent to form an amic acid, reducing the amount of basic nitrogen present in the dispersant. The use of higher or lower succinic to primary amine stoichiometrics or polyalkene molecular weights may lead to the formation of significant amounts of sediment. Very large polyamines (>$N_8$) should be avoided as the use thereof can result in a higher than acceptable hydrophilic to hydrophobic load, which can cause the borated dispersant to fall out of solution.

The functionality of the polyalkenyl succinic acylating agent from which the polyalkenyl succinimide used in the process of the present invention is derived is preferably from about 0.8 to about 1.8, such as from about 0.9 to about 1.7, more preferably from about 1.1 to about 1.6. When the functionality of the polyalkenyl succinic acylating agent (the average number of acylating moieties per polyalkene or functionality) is too high (e.g., >2), the borated succinimide dispersant concentrate product may be too viscous and may cause the borated dispersant complex to be insufficiently soluble in oil causing sediment (sediment can include both a fraction of the borated dispersant complex and excess boric acid). On the other hand, a functionality that is too low (e.g., <0.5) can limit the total concentration of boric acid that can be stabilized by the dispersant carrier molecules. Functionality (F) can be determined according to the following formula:

$$F=(SAP \times M_n)/((1122 \times A.I.)-(SAP \times MW))$$

wherein SAP is the saponification number (i.e., the number of milligrams of KOH consumed in the complete neutralization of the acid groups in one gram of the succinic-containing reaction product, as determined according to ASTM D94); $M_n$ is the number average molecular weight of the starting polyalkene (e.g., polybutene); A.I. is the percent active ingredient of the succinic-containing reaction product (the remainder being unreacted polyalkene and diluent); and MW is the molecular weight of the acyl group-producing moiety (98 for maleic anhydride). Generally, each succinic group will react with a segment of the polyamine moiety and the number of succinic groups in the PIBSA will determine the number of polyamine groups in the dispersant. Preferably, the polyalkenyl succinimide used in the process of the present invention has been stripped or otherwise treated to remove water of the amination reaction.

The boron source used in the process of the present invention is orthoboric acid. The boric acid is conveniently introduced in the form of a boric acid slurry in a substantially nonprotic hydrocarbon medium, such as diluent oil.

In accordance with the process of the present invention, the boric acid slurry is added to a polyalkenyl succinimide (also preferably in a substantially nonprotic hydrocarbon medium, such as diluent oil) in an amount resulting in a molar ratio of boron to nitrogen of from about 2:1 to about 5:1, preferably from about 2.2:1 to about 4:1, such as from about 2.5:1 to about 3.5:1, to form a mixture.

The mixture is then heated under conditions (at a temperature and pressure and for a time) sufficient to remove from the reaction mixture from about 0.8 to about 1.2 moles of water of reaction per mole of boric acid charged, preferably under conditions sufficient to remove from the reaction mixture from about 0.9 to about 1.1 moles of water of reaction per mole of boric acid charged, more preferably under conditions sufficient to remove from the reaction mixture about 1.0 moles of water of reaction per mole of boric acid charged. To remove this amount of water of reaction, the reaction mixture may, for example, be heated (at atmospheric pressure) to a temperature in the range of from about 125° C. to about 200° C., preferably from about 140° C. to about 180° C., such as from about 150° C. to about 170° C., for from about 1 to about 5 hours, with mixing (e.g., stirring or shaking) under an inert atmosphere (e.g., using a nitrogen sweep). Heating may be accompanied by nitrogen stripping to facilitate the removal of water.

The resulting borated dispersant concentrate has a molar ratio of boron to nitrogen of from about 2.1:1.0 to about 5.0:1.0, preferably from about 2.2:1.0 to about 4.0:1.0, such as from about 2.5:1.0 to about 3.5:1.0, a boron content of from about 1.0 mass % to about 5.0 mass %©, preferably from about 1.5 mass %© to about 4.0 mass %©, more preferably from about 2.0 to about 3.0 mass %, based on the total mass of the borated dispersant concentrate, including associated diluent oil and, in an unfiltered form, preferably has a sediment content of less than about 0.3 vol %, such as less than about 0.2 vol %, more preferably less than about 0.1 vol %, based on the total volume of the borated dispersant concentrate, including associated diluent oil. Preferably, the borated dispersant concentrate has a molar ratio of boron to theoretical basic nitrogen of from about 3:1 to about 7:1, preferably from about 3:1 to about 6.5:1, such as from about 3.2:1 to about 6:1. As used herein, the term "basic nitrogen" refers to nitrogen in the form of an amine, as opposed to an amide or imide in the starting dispersant.

The amount of basic nitrogen of the dispersant can be estimated by subtracting the equivalents of nitrogen present as imide and amide from the total equivalents of nitrogen in the dispersant. The equivalents of nitrogen present as imide and amide can, in turn, be estimated from the stoichiometric ratio of succinic groups charged to amine groups in the polyamine. Theoretical basic nitrogen can be determined according to the following formula:

Theoretical basic nitrogen=total moles of nitrogen in
the borated dispersant−moles of SA charged
(that react with the nitrogen in the PAM).

The amount of basic nitrogen of the dispersant can also be determined by TBN titration in accordance with the procedures of ASTM D4739. Using the procedures of ASTM D4739 results in higher boron to basic nitrogen ratios than theoretical, meaning that not all of the nitrogen in the borated dispersant titrates. Since metaboric acid is a weaker acid than the hydrochloric acid used in the titration method, this method should measure at least those basic nitrogen atoms that are coordinated to boric acid and therefore provides a more accurate determination of boron to basic nitrogen molar ratio than a theoretical value.

The borated dispersant concentrate of the present invention preferably has a kinematic viscosity at 100° C. of less than about 700 cSt, preferably less than about 500 cSt, more preferably less than about 300 cSt, and an active ingredient content of greater than about 15 mass %, such as greater than 30 mass %, or greater than about 40 mass %, wherein the active ingredient (A.I.) content of the concentrate is determined as follows:

A.I.=(concentration of acylating agent×mass acylat-
ing agent+mass amine−water of amination reac-
tion+concentration of borating agent slurry×
mass slurry−water of boration reaction (e.g., 1
mole H₂O per mole orthoboric acid))/theoretical
mass of product.

The borated dispersant concentrates of the present invention should, without filtering, provide a sediment content of less than 0.3 vol %©, such as less than 0.2 vol %, preferably less than 0.1 vol % or 0.05 vol %. As used herein, the sediment level is that determined by by diluting a sample of the borated dispersant concentrate 50:50 by volume with heptane, centrifuging the sample in a graduated sediment tube and reading the volume of solid material against the graduations. The reading is then multiplied by 2 to account for the dilution and expressed as percentage by volume.

The borated dispersant concentrate may be used to formulate a lubricating oil composition by adding said borated dispersant concentrate to the lubricating oil composition in an amount introducing from about 20 to about 600 ppm, such as from about 40 to about 400 ppm, or from about 60 to about 300 ppm of boron.

This invention will be further understood by reference to the following examples, wherein all parts are parts by weight, unless otherwise noted and which include preferred embodiments of the invention.

EXAMPLES

Example 1 (Invention)

To a mixture of polyisobutenyl (Mn—950 Da) succinic anhydride (300 g) having a functionality (F) of 1.2 and Group I diluent oil (132 g) at 145-150° C. and under nitrogen was added PAM (27 g) (a commercial polyamine bottoms product having, on average, 6.5 nitrogens per molecule, a nitrogen content of about 34 mass %, a molecular weight of about 275 daltons and an equivalent weight of primary amine of about 115 (by titration, 8.7 meq primary amine/g)). The mixture was heated to 155° C. for 2 hours with stirring. A 30% slurry was prepared by intimately mixing orthoboric acid (195 g) with diluent oil (455 g) in a laboratory blender. The reaction mixture was heated to 160° C. The slurry (287 g) was added dropwise to the reaction mixture, after which the mixture was heated to 160° C. for 2 hours. A nitrogen sparge was applied to the reaction mixture over the subsequent 1 hour at 160° C. to yield borated polyisobutenyl succinimide dispersant.

Examples 2 Through 4 (Invention)

Compositions were prepared as in Example 1 with the charge masses of slurry increasing to 333 g (Example 2), 384 g (Example 3), and 442 g (Example 4).

Example 5 (Invention)

To a mixture of polyisobutenyl (Mn—950 Da) succinic anhydride (625 g,) and Group II+ diluent oil (317 g) at 157° C. and under nitrogen was added PAM (46 g) (as in Example 1). The mixture was heated to 157° C. for 3 hours with stirring. A 34% slurry was prepared by shaking orthoboric acid (127 g) with base oil (248 g) in a Duran bottle at 60° C. A 400 g aliquot of the reaction mixture was removed and the remaining reaction mixture was heated to 170 C. The boric acid slurry was added portion-wise to the reaction mixture and Group II+ diluent oil (50 g) was used to rinse the bottle into the reactor. The mixture was then stirred at 170° C. for 1 hour. A nitrogen sparge was applied to the reaction mixture over the subsequent 2 hours at 170° C. to yield borated polyisobutenyl succinimide dispersant composition.

Example 6 (Invention)

A composition was prepared in the same manner as in Example 5 with a PAM charge of 71 g, and a boric acid slurry charge of 390 g to yield a borated polyisobutenyl succinimide dispersant composition.

Examples 7 and 8 (Invention)

Compositions were prepared as in Examples 2 and 4, respectively, using a slurry prepared by shaking, not blending (as in Examples 5 and 6), and a boration temperature of 170° C.

Example 9 (Comparative)

A composition was prepared as in Example 1, using polyisobutenyl (Mn—1300 Da) succinic anhydride (with charge masses adjusted accordingly).

Example 10 (Invention)

A composition was prepared as in Example 9, using polyisobutenyl (Mn—1900 Da) succinic anhydride (with charge masses adjusted accordingly).

Example 11 (Comparative)

A composition was prepared as in Example 9, using polyisobutenyl (Mn—2225 Da) succinic anhydride (with charge masses adjusted accordingly).

Example 12 (Comparative)

A composition was prepared as in Example 9, using polyisobutenyl (Mn—450 Da) succinic anhydride (with charge masses adjusted accordingly).

Example 13 (Comparative)

A composition was prepared as in Example 12, using polyisobutenyl (Mn—700 Da) succinic anhydride (with charge masses adjusted accordingly).

Example 14 (Inventive)

A composition was prepared, as in Example 1, using TEPA (an $N_5$ amine) as the polyamine (with charge masses adjusted accordingly).

Examples 15 Through 19 (Comparative)

Compositions were prepared, as in Example 1, using polyisobutenyl (Mn—2225 Da) succinic anhydride borated to provide boron to total nitrogen molar ratios of from 0 to 1.14 (with charge masses adjusted accordingly).

Examples 20 Through 23 (Comparative)

Compositions were prepared, as in Example 1, using polyisobutenyl (Mn—1900 Da) succinic anhydride borated to provide boron to total nitrogen molar ratios of from 0 to 0.69 (with charge masses adjusted accordingly).

The composition and properties of the exemplified materials are summarized below, in Tables 1 and 2.

TABLE 1

| Ex | Inv/Comp | CR | B mass % | N mass % | Al mass % | $kv_{100}$ cSt | Sed vol % | B; total N molar ratio | B; basic N molar ratio | B:titrated N molar ratio ASTM D4739 |
|---|---|---|---|---|---|---|---|---|---|---|
| 1 | Inv | 0.99 | 2.05 | 1.28 | 43 | 218 | 0.04 | 2.07 | 3.3* | — |
| 2 | Inv | 0.99 | 2.31 | 1.23 | 42 | 259 | 0.04 | 2.44 | 3.8* | — |
| 3 | Inv | 0.99 | 2.67 | 1.17 | 41 | 242 | 0.07 | 2.95 | 4.6* | — |
| 4 | Inv | 0.99 | 2.65 | 1.08 | 40 | 184 | 0.20 | 3.18 | 5.1* | — |
| 5 | Inv | 1.24 | 2.25 | 0.98 | 41 | 179 | 0.10 | 2.97 | 5.5* | 7.8 |
| 6 | Inv | 0.80 | 2.30 | 1.47 | 41 | 287 | 0.30 | 2.03 | 2.9* | 4.2 |
| 7 | Inv | 1.00 | 2.21 | 1.18 | 41 | 202 | 0.02 | 2.43 | 3.8* | 5.5 |
| 8 | Inv | 1.00 | 2.52 | 0.94 | 39 | 188 | 0.20 | 3.47 | 5.5* | 7.5 |

*calculated

TABLE 2

| Ex | Inv/Comp | PIB mw | Amine | F | CR | B mass % | N mass % | Al mass % | kv$_{100}$ cSt | Sed vol % | B:total N molar ratio | B:titrated N molar ratio ASTM D4739 |
|---|---|---|---|---|---|---|---|---|---|---|---|---|
| 9  | Comp | 1300 | PAM | 1.74 | 1.00 | 1.70 | 1.72 | 46* | 537  | 0.15 | 1.28  | 3.2 |
| 10 | Comp | 1900 | PAM | 1.42 | 1.00 | 0.48 | 1.25 | 51* | 801  | 0.15 | 0.49  | — |
| 11 | Comp | 2225 | PAM | 1.55 | 1.00 | 0.27 | 1.18 | 50* | 732  | 0.15 | 0.30  | — |
| 12 | Comp | 450  | PAM | 1.18 | 1.06 | 3.07 | 2.37 | 50* | 290  | 4.00 | 1.65  | — |
| 13 | Comp | 700  | PAM | 1.05 | 1.06 | 2.68 | 1.79 | 55* | 483  | 0.55 | 1.90  | — |
| 14 | Inv  | 1000 | N$_5$ | 1.26 | 0.96 | 2.64 | 1.34 | 47* | 429  | 0.07 | 2.50  | — |
| 15 | Comp | 2225 | PAM | 1.55 | 1.00 | 0.00 | 1.24 | 52* | 508  | 0.01 | 0.00  | — |
| 16 | Comp | 2225 | PAM | 1.55 | 1.00 | 0.26 | 1.17 | 50* | 571  | 0.06 | 0.29  | — |
| 17 | Comp | 2225 | PAM | 1.55 | 1.00 | 0.46 | 1.11 | 49* | 1080 | 0.02 | 0.53  | — |
| 18 | Comp | 2225 | PAM | 1.55 | 1.00 | 0.67 | 1.08 | 48* | 2194 | 0.03 | 0.81  | — |
| 19 | Comp | 2225 | PAM | 1.55 | 1.00 | 0.00 | 1.02* | 47* | GEL | —† | 1.14* | — |
| 20 | Comp | 1900 | PAM | 1.55 | 1.00 | 0.00 | 1.37 | 53* | 535  | 0.01 | 0.11  | — |
| 21 | Comp | 1900 | PAM | 1.42 | 1.00 | 0.30 | 1.33 | 52* | 664  | 0.10 | 0.29  | — |
| 22 | Comp | 1900 | PAM | 1.42 | 1.00 | 0.48 | 1.25 | 51* | 801  | 0.15 | 0.49  | — |
| 23 | Comp | 1900 | PAM | 1.42 | 1.00 | 0.68 | 1.26 | 50* | 1048 | 0.03 | 0.69  | — |

*calculated;
†too viscous to measure

Examples 1 through 8 demonstrate that the process of the present invention provides a borated dispersant composition having a boron to total nitrogen molar ratio of more than 2, with an acceptable amount of sediment, not requiring the filtration of the product before use.

The importance of maintaining a moderate polymer molecular weight to avoid the production of sediment, despite the enhanced solubility of the hydrophobic chain with increasing molecular weight, can be seen by comparing Example 9 to Examples 1 through 4. Specifically, Example 9 demonstrates that with a polyisobutylene alkyl group of Mn 1300 Da, the sediment volume in the borated alkylsuccinimide product is 0.15 vol % at a boron to total nitrogen molar ratio of only 1.28. This can be compared directly to Examples 1 through 4, where the alkyl group is polyisobutylene of Mn 950 Da, and where the sediment volume does not reach 0.15 vol % until boron to total nitrogen molar ratios of between 2.95 and 3.18 are reached. When the Mn of the polyisobutylene alkyl group is higher 1900 (Example 10) or 2225 Da (Example 11), equal sediment values of 0.15 vol % are seen at boron to total nitrogen molar ratios of only 0.56 and 0.34, respectively. This is possibly due to the difference in the aggregation properties of the succinimide dispersant as a function of molecular weight, which in turn impacts the ability of the succinimide dispersant to interact with the boron containing moiety.

If the polymer molecular weight is too low, the hydrophilic to hydrophobic load becomes excessively high. Example 12 shows that for a borated polyisobutenyl succinimide dispersant where the polyisobutenyl group has a molecular weight of 450 Da, at a boron to total nitrogen molar ratio of only 1.65, the sediment volume is 4 vol %. At the larger Mn of 700, Example 13 shows that a higher boron to total nitrogen molar ratio of 1.9 gives a lower sediment volume of 0.55 mass %; however, this remains dis-advantageously high and would require a processing step such as filtration before use in lubricating oil formulations.

Conversely, at high molecular weights, even at low B to total N molar ratios, the viscosity of the composition increases substantially, which is disadvantageous for logistical reasons such as ease of pumping. Examples 15 to 18 show an increase in kv$_{100}$ of a polyalkenyl succinimide dispersant from 508 cSt at 100° C. as boric acid is introduced, with a composition with a boron to total nitrogen molar ratio of 0.81 having a kv$_{100}$ of 2194 cSt at 100° C. Example 19 demonstrates that a combination of high MW and moderate boron to total nitrogen molar ratio of only 1.14 caused the composition to undergo gelation; gelation prohibits pumpability and renders the product useless for lubricating oil formulations.

Examples 20 through 23 demonstrate the increase in viscosity as the boron to total nitrogen molar ratio increases in a polyisobutylene succinimide dispersant series where the polyalkenyl (polyisobutene) molecular weight is 1900 Da. The rate of viscosity growth with the 1900 molecular weight materials is slower than that of the 2225 molecular weight material, however, the preference for low viscosity products drives to preferentially lower MW alkyl groups in borated polyalkyl succinimide compositions.

The amine size is also an important consideration. Specifically, the amine needs to be large enough to solubilize the hydrophilic load, requiring sizes >N$_3$ (preferably >N$_5$). Example 14 shows that a polyisobutenyl succinimide dispersant formed by the reaction of polyisobutenyl succinic anhydride and TEPA (an N$_5$ amine), when borated to a boron to total nitrogen molar ratio of 2.5, contains only 0.07 vol % sediment. Smaller amines (<N$_4$) should be avoided because the ability of the dispersant to solubilize boric acid is reduced. Very large amines (>N$_8$) should be avoided as well, because the hydrophilic to hydrophobic load gets excessively high, causing the dispersant complex to come out of solution.

It should be noted that the compositions of this invention comprise defined, individual, i.e., separate, components that may or may not remain the same chemically before and after mixing. Thus, it will be understood that various components of the composition, essential as well as optional and customary, may react under the conditions of formulation, storage or use and that the invention also is directed to, and encompasses, the product obtainable, or obtained, as a result of any such reaction.

The disclosures of all patents, articles and other materials described herein are hereby incorporated, in their entirety, into this specification by reference. The principles, preferred embodiments and modes of operation of the present invention have been described in the foregoing specification. What applicants submit is their invention, however, is not to be construed as limited to the particular embodiments disclosed, since the disclosed embodiments are regarded as illustrative rather than limiting. Changes may be made by those skilled in the art without departing from the spirit of the invention.

What is claimed is:

1. A process for producing a borated polyalkenyl succinimide dispersant composition in which the boron is incorporated primarily as cyclic metaboric acid moieties and the equivalents of boron incorporated per equivalent of nitrogen in the succinimide carrier is greater than 2; said process comprising the steps of adding a slurry of orthoboric acid in a substantially non-protic hydrocarbon medium to a polyalkenyl succinimide in a substantially non-protic hydrocarbon medium to form a reaction mixture, and heating said reaction mixture under conditions sufficient to remove from the reaction mixture from about 0.8 to about 1.2 moles of water of reaction per mole of boric acid charged, wherein said polyalkenyl succinimide is derived from a reaction of a polyalkenyl succinic acylating agent derived from a polyalkene having a number average molecular weight (Mn) of from about 700 to about 1600 daltons and a polyamine or polyamine mixture having, or having on average, from about 5 to about 8 nitrogen atoms per molecule, the succinic to primary amine stoichiometric ratio of said polyalkenyl succinimide being no greater than about 1.3.

2. The process of claim 1, wherein said polyalkene has a number average molecular weight (Mn) of from about 700 to about 1400 daltons.

3. The process of claim 2, wherein said polyalkene has a number average molecular weight (Mn) of from about 800 to about 1250 daltons.

4. The process of claim 1, wherein said polyamine or polyamine mixture has, or has on average, from about 6 to about 7 nitrogen atoms per molecule.

5. The process of claim 1, wherein said polyalkenyl succinimide has a succinic to primary amine stoichiometric ratio of from about 0.8 to about 1.3.

6. The process of claim 5, wherein said polyalkenyl succinimide has a succinic to primary amine stoichiometric ratio of from about 0.9 to about 1.12.

7. The process of claim 6, wherein said polyalkenyl succinimide has a succinic to primary amine stoichiometric ratio of from about 0.9 to about 1.1.

8. The process of claim 1, wherein said polyalkenyl succinic acylating agent from which said polyalkenyl succinimide is derived has a functionality of from about 0.8 to about 1.8.

9. The process of claim 1, wherein said polyalkenyl succinic acylating agent from which said polyalkenyl succinimide is derived has a functionality of from about 1.1 to about 1.6.

10. The process of claim 1, wherein said slurry of orthoboric acid is added to said polyalkenyl succinimide in an amount resulting in a boron to nitrogen molar ratio of from about 2:1 to about 5:1.

11. The process of claim 10, wherein said slurry of orthoboric acid is added to said polyalkenyl succinimide in an amount resulting in a boron to nitrogen molar ratio of from about 2.5:1 to about 3.5:1.

12. The process of claim 1, wherein said reaction mixture is heated under conditions sufficient to remove from the reaction mixture from about 0.9 to about 1.1 moles of water of reaction per mole of boric acid charged.

13. The process of claim 12, wherein said reaction mixture is heated under conditions sufficient to remove from the reaction mixture about 1.0 moles of water of reaction per mole of boric acid charged.

14. The process of claim 1, wherein said reaction mixture is heated to a temperature in the range of from about 125° C. to about 200° C. for about 1 to about 5 hours.

15. A borated polyalkenyl succinimide dispersant composition formed by the process of claim 1.

16. A borated polyalkenyl succinimide dispersant composition formed by the process of claim 10.

17. A borated polyalkenyl succinimide dispersant composition formed by the process of claim 12.

18. A borated polyalkenyl succinimide dispersant composition formed by the process of claim 14.

19. A borated polyalkenyl succinimide dispersant composition comprising polyalkenyl succinimide is derived from a reaction of a polyalkenyl succinic acylating agent derived from a polyalkene having a number average molecular weight (Mn) of from about 700 to about 1600 daltons and a polyamine or polyamine mixture having, or having on average, from about 5 to about 8 nitrogen atoms per molecule, and a succinic to primary amine stoichiometric ratio of no greater than about 1.3, wherein said polyalkenyl succinimide dispersant has associated therewith, boron, wherein said the boron is associated primarily as cyclic metaboric acid moieties and the equivalents of boron incorporated per equivalent of nitrogen in the succinimide dispersant is greater than about 2.

20. The borated polyalkenyl succinimide dispersant composition of claim 19, wherein said polyalkene has a number average molecular weight (Mn) of from about 700 to about 1400 daltons.

21. The borated polyalkenyl succinimide dispersant composition of claim 20, wherein said polyalkene has a number average molecular weight (Mn) of from about 800 to about 1250 daltons.

22. The borated polyalkenyl succinimide dispersant composition of claim 19, wherein said polyamine or polyamine mixture has, or has on average, from about 6 to about 7 nitrogen atoms per molecule.

23. The borated polyalkenyl succinimide dispersant composition of claim 19, wherein said polyalkenyl succinimide has a succinic to primary amine stoichiometric ratio of from about 0.8 to about 1.3.

24. The borated polyalkenyl succinimide dispersant composition of claim 23, wherein said polyalkenyl succinimide has a succinic to primary amine stoichiometric ratio of from about 0.9 to about 1.12.

25. The borated polyalkenyl succinimide dispersant composition of claim 24, wherein said polyalkenyl succinimide has a succinic to primary amine stoichiometric ratio of from about 0.9 to about 1.1.

26. The borated polyalkenyl succinimide dispersant composition of claim 19, wherein said polyalkenyl succinic acylating agent from which said polyalkenyl succinimide is derived has a functionality of from about 0.8 to about 1.8.

27. The borated polyalkenyl succinimide dispersant composition of claim 26, wherein said polyalkenyl succinic acylating agent from which said polyalkenyl succinimide is derived has a functionality of from about 1.1 to about 1.6.

28. A borated polyalkenyl succinimide dispersant composition of claim 19, having a molar ratio of boron to nitrogen of from about 2.1:1 to about 5.0:1.

29. A borated polyalkenyl succinimide dispersant composition of claim 28, having a molar ratio of boron to nitrogen of from about 2.2:1 to about 4.0:1.

30. A borated polyalkenyl succinimide dispersant composition of claim 29, having a molar ratio of boron to nitrogen of from about 2.5:1 to about 3.5:1.

31. A borated polyalkenyl succinimide dispersant composition of claim 19, having a boron content of from about 1.0 mass % to about 5.0 mass %©, based on the total mass of the composition.

32. A borated polyalkenyl succinimide dispersant composition of claim 31, having a boron content of from about 1.5 mass % to about 4.0 mass %, based on the total mass of the composition.

33. A borated polyalkenyl succinimide dispersant composition of claim 32, having a boron content of from about 2.0 mass % to about 3.0 mass %, based on the total mass of the composition.

34. A borated polyalkenyl succinimide dispersant composition of claim 19, having a sediment content of less than about 0.3 vol %, based on the total volume of the composition.

35. A borated polyalkenyl succinimide dispersant composition of claim 34, having a sediment content of less than about 0.1 vol %, based on the total volume of the composition.

36. A borated polyalkenyl succinimide dispersant composition of claim 19, having a molar ratio of boron to theoretical basic nitrogen of from about 3:1 to about 7:1.

37. A borated polyalkenyl succinimide dispersant composition of claim 36, having a molar ratio of boron to theoretical basic nitrogen of from about 3.2:1 to about 6:1.

38. A borated polyalkenyl succinimide dispersant composition of claim 19, having a kinematic viscosity at 100° C. of less than about 700 cSt.

39. A borated polyalkenyl succinimide dispersant composition of claim 38, having a kinematic viscosity at 100° C. of less than about 500 cSt.

40. A borated polyalkenyl succinimide dispersant composition of claim 19, having an active ingredient content of greater than about 15 mass %.

41. A borated polyalkenyl succinimide dispersant composition of claim 40, having an active ingredient content of greater than about 40 mass %.

42. A lubricating oil composition comprising an amount of the borated polyalkenyl succinimide dispersant composition of claim 19 providing from about 20 to about 600 ppm of boron, based on the total mass of said lubricating oil composition.

* * * * *